United States Patent [19]
Hötzel et al.

[11] Patent Number: 5,494,557
[45] Date of Patent: Feb. 27, 1996

[54] METHOD OF OPERATING AN OXYGEN PROBE HAVING AN INTERNAL REFERENCE ATMOSPHERE

[75] Inventors: Gerhard Hötzel, Stuttgart; Harald Neumann, Vaihingen; Walter Strassner, Schorndorf; Johann Riegel, Bietigheim-Bissingen, all of Germany

[73] Assignee: Robert Bosch GmbH, Stuttgart, Germany

[21] Appl. No.: 316,108

[22] Filed: Sep. 30, 1994

[30] Foreign Application Priority Data

Sep. 30, 1993 [DE] Germany .................. 43 33 231.5

[51] Int. Cl.⁶ ............................................. G01N 27/407
[52] U.S. Cl. .................. 205/784; 204/425; 204/426; 204/427
[58] Field of Search .................. 204/153.18, 421–429

[56] References Cited

U.S. PATENT DOCUMENTS

| | | | |
|---|---|---|---|
| 4,440,621 | 4/1984 | Kitahara et al. | 204/425 |
| 4,502,939 | 3/1985 | Holfelder et al. | 204/426 |
| 4,615,787 | 10/1986 | Yamada et al. | 204/425 |
| 4,702,816 | 10/1987 | Hashimoto et al. | 204/425 |
| 4,818,362 | 4/1989 | Asakura et al. | 204/426 |

FOREIGN PATENT DOCUMENTS

| | | |
|---|---|---|
| 0035177 | 9/1981 | European Pat. Off. . |
| 0082372 | 6/1983 | European Pat. Off. . |
| 0079085 | 5/1993 | European Pat. Off. . |
| 2194056 | 2/1988 | United Kingdom . |
| 2219093 | 11/1989 | United Kingdom . |
| 2276458 | 9/1994 | United Kingdom . |

*Primary Examiner*—T. Tung
*Attorney, Agent, or Firm*—Walter Ottesen

[57] ABSTRACT

The invention is directed to a method of operating an exhaust-gas probe having a pumped reference atmosphere in a relatively closed volume. In this method, the oxygen ion current, which carries the pump current Ip to the reference atmosphere, is temporarily increased under specific conditions. In this way, an adulteration of the reference atmosphere can be more rapidly eliminated. This adulteration can occur because of fuel particles which diffuse in.

8 Claims, 4 Drawing Sheets

METHOD OF OPERATING AN OXYGEN PROBE HAVING AN INTERNAL REFERENCE ATMOSPHERE

FIELD OF THE INVENTION

The invention relates to a method for eliminating the adulteration of the reference atmosphere during operation of an oxygen probe equipped with a pumped internal reference atmosphere.

BACKGROUND OF THE INVENTION

An oxygen probe of this kind is disclosed, for example, in U.S. Pat. No. 4,496,455. The oxygen probe described in this patent includes a measuring cell and a pump cell. The measuring cell is formed by an electrolyte having a measuring electrode and a reference electrode. The pump cell is configured by a further electrode pair on the same electrolyte. The measuring electrode is exposed to the exhaust gas of an internal combustion engine and the reference electrode is subjected to a reference atmosphere in a small volume within the exhaust-gas probe. This volume communicates with the exhaust gas or the ambient only via small bores via which an overpressure within the small volume can be reduced as may be required.

However, such a reference volume is not gas-tight with respect to the ambient or the exhaust gas because of these bores as well as a residual porosity of the electrolyte. A voltage is applied to the electrodes of the pump cell to maintain a stable reference atmosphere. This voltage is so dimensioned and directed that oxygen ions from the exhaust gas are pumped into the reference volume. Such an internal pumped reference atmosphere has the advantage with respect to an ambient air reference that an unwanted change of its composition is comparatively low. Such a change in composition can occur, for example, because of water spray or fuel. Adulterations of this kind can, however, occur especially at standstill of the engine. For example, fuel particles from the exhaust gas or from the ambient can diffuse into the reference atmosphere and there bind oxygen particles. In this case, the partial pressure of the reference oxygen drops which leads to the condition that the voltage of the measuring cell drops and even changes the sign in dependence upon the intensity of the contamination of the reference atmosphere with fuel particles. The probe signal made incorrect in this case increases the emission of unwanted exhaust-gas particles because of its influence on the mixture formation of the engine.

SUMMARY OF THE INVENTION

It is an object of the invention to provide a method and an apparatus for rapidly eliminating an adulteration of the reference atmosphere.

The method of the invention is for operating an exhaust-gas probe including an oxygen-ion conducting solid electrolyte, a measuring electrode subjected to the exhaust gas; holding means for holding a reference gas; and, a reference electrode subjected to the reference gas; the reference gas defining an internal reference by being partitioned off from the exhaust gas and the ambient so as to make a particle exchange between the reference gas and the exhaust gas and/or the ambient at least difficult. The method includes the steps of: continuously applying a voltage across the measuring and reference electrodes to have a predetermined magnitude and direction so as to cause a pump current (Ip) to flow between the electrodes for transporting oxygen ions from the measuring electrode to the reference electrode without causing the electrolyte to decompose under the action of the continuously applied voltage; and, temporarily increasing the pump current (Ip) for a first time duration to values which could otherwise lead to a decomposition of the electrolyte if allowed to act on the electrolyte over a second time duration greater than the first time duration.

The increase in pump current can be triggered after each start of the internal combustion engine or after an elapse of pregiven operation durations of the engine and/or in specific operating states of the engine. This increase in pump current can be triggered, for example, when a drop of the output voltage Us of the exhaust-gas probe indicates an adulterated reference atmosphere or when the output voltage of the exhaust gas probe does not at least once pass through a pregiven threshold value within a pregiven time span.

It is advantageous to match the product of the duration of the temporary current increase and the amount of the current increase to the magnitude of the reference volume.

The invention can also be applied to a more complexly configured sensor having additional electrode pairs. Here, the pump current is then increased temporarily in the arrangement supplying the Nernst voltage.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
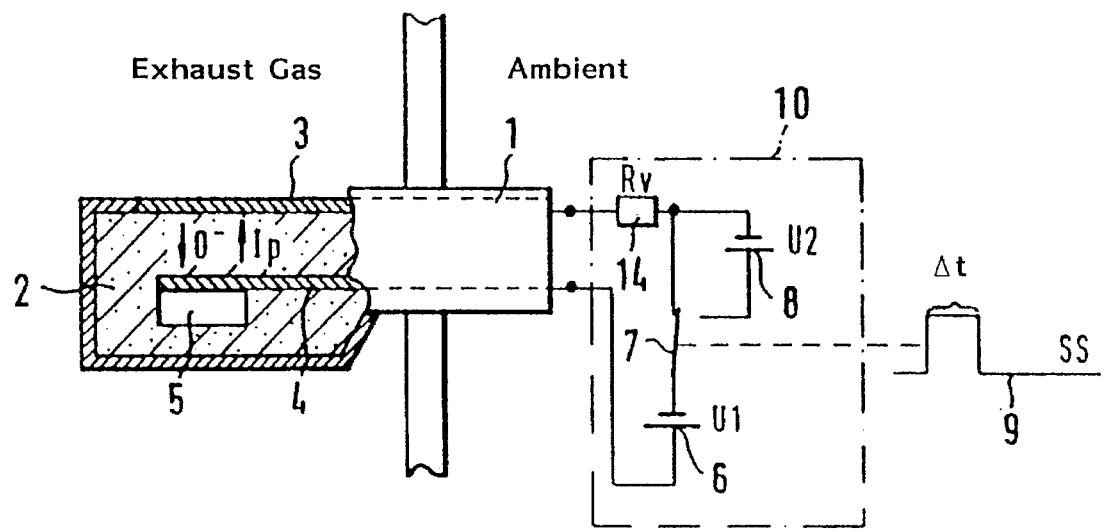
FIG. 1 is a schematic of an exhaust-gas probe having a pumped reference and an embodiment of a circuit suitable for carrying out the method of the invention.

Reference numeral 1 in FIG. 1 identifies an exhaust-gas probe having a solid electrolyte 2 which conducts oxygen ions. The solid electrolyte 2 is subjected to the exhaust gas of an internal combustion engine via a measuring electrode 3 and is subjected to a reference atmosphere in a small volume 5 within the exhaust-gas probe via reference electrode 4. This arrangement operates as an oxygen concentration cell in accordance with the Nernst principle and supplies the step-shaped output signal known per se in dependence upon the logarithm of the quotient of the oxygen concentration in the exhaust gas and the small volume.

To maintain a stable reference atmosphere, a voltage U1 is applied to the measuring electrode 3 and the reference electrode 4 by means of a first voltage source 6 via a series resistor (Rv) 14 during normal operation of the exhaust-gas probe. The voltage U1 is so directed that oxygen ions are pumped from the exhaust gas into the small volume. For this purpose, the positive pole of the voltage source 6 is connected to the reference electrode and the negative pole to the measuring electrode 3.

This voltage is applied in continuous operation and can, for example, be selected to be greater than the highest possible Nernst voltage of the concentration cell. With the voltage applied in this manner, a decomposition of the electrolyte is substantially avoided on the one hand and, on the other hand, even for a rich mixture (that is, oxygen deficient exhaust gas), an impermissible effect on the oxygen-rich reference atmosphere by diffusion of oxygen out of the reference atmosphere is prevented.

To eliminate an adulterated reference atmosphere, the oxygen ionic current can be increased temporarily to the reference gas volume in accordance with this embodiment in that the switch 7 is so actuated with a control signal SS (9) for a limited time Δt that a voltage U1+U2 is applied to the exhaust-gas probe. The voltage U2 is supplied from a second voltage source 8. As an alternative to the series circuit of U1 and U2, a switchover can be made to a single voltage source U2 wherein U2>U1. The block 10 shown with a broken line encloses the two voltage sources 6 and 8 and the switch 7 as well as the series resistor 14 to show an arrangement for supplying current with a controllable output current Ip.

A porous channel can, for example, be provided extending from the reference gas volume to the ambient in order to prevent that the oxygen ionic current to the reference gas volume leads to an unwanted high pressure in the reference gas volume. Such a channel, which permits a particle flow caused by a pressure drop from the reference volume to the ambient, can be also realized by a reference electrode feed line to the external contacts of the exhaust-gas probe with this reference electrode feed line being configured to be porous.

Figure 2:
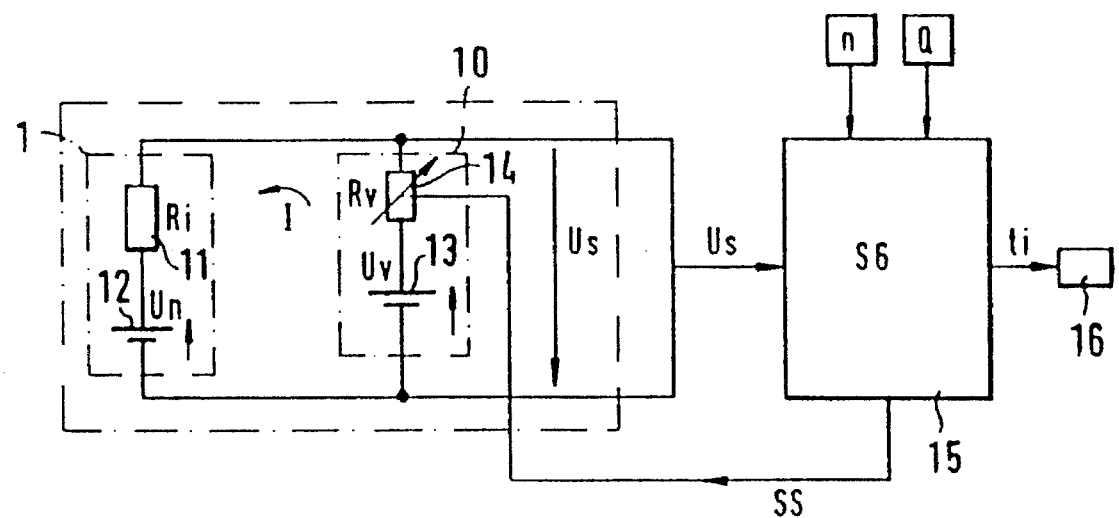
FIG. 2 is an equivalent circuit of the probe and a further embodiment of a circuit which is suitable for carrying out the method of the invention with the circuit being shown together with a control apparatus.

The equivalent circuit diagram of FIG. 2 shows the exhaust-gas probe 1 as a series circuit comprising an internal resistance (Ri) 11 and a source voltage (Un) 12 corresponding to the voltage which is present between the measuring electrode and the reference electrode as a consequence of the different oxygen partial pressures in the exhaust gas and in the reference gas volume. The voltage supply 10 is connected in opposition to the exhaust-gas probe. This supply voltage 10 comprises a bias voltage source 13 and a controllable series resistor (Rv) 14.

The control signal SS for adjusting the series resistor Rv comes from a control apparatus 15, for example, a computer which is conventionally available for an internal combustion engine. The computer operates, inter alia, to output injection pulses ti to injection devices 16. These injection pulses ti are formed in dependence upon operating parameters of the engine such as the rpm (n), the load Q and the signal Us of the exhaust-gas probe.

Figure 2A:
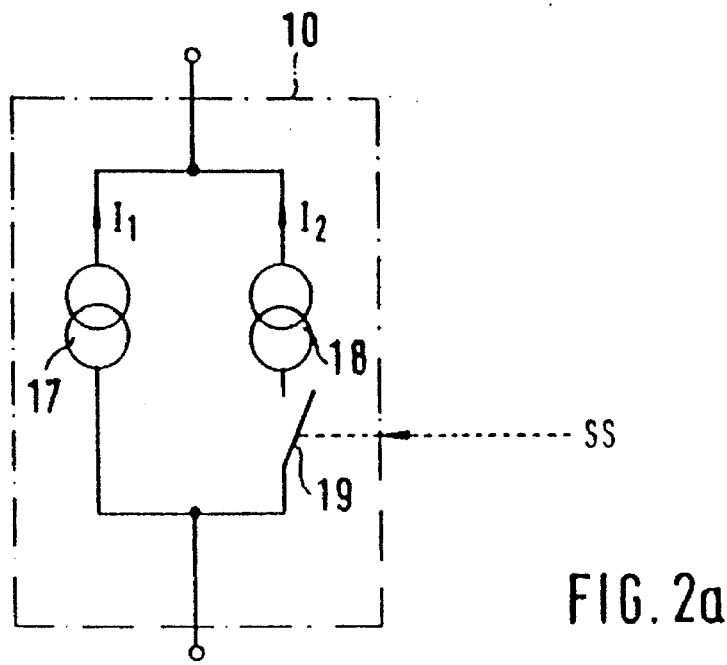
FIG. 2a is a schematic of the voltage supply shown in FIG. 2.

FIG. 2a shows, as a further embodiment, a voltage supply 10 comprising a constant current source 17 and a further constant current source 18. The current source 18 is connected via a switch 19 which is controlled by a switching signal SS. The constant current source 17 supplies the pump current I1 for the normal operation of the exhaust-gas probe and the constant current source 18 supplies an additional pump current I2 for eliminating an adulterated reference atmosphere.

The conditions under which the control apparatus 15 emits a signal SS for increasing the oxygen ionic current to the reference gas volume can vary considerably. For example, it is conceivable that the reference gas volume is scavenged with an increased oxygen ionic current after each start of the engine or after a pregiven operating duration of the engine has elapsed and/or in specific operating states of the engine such as in overrun operation.

The behavior of the voltage Us can be used as a trigger criterium in the context of the embodiment of FIG. 2 for increasing the pump voltage or the pump current. The following relationship applies for the voltage Us for the embodiment of FIG. 2:

$$Us = Uv - Ip*Rv = Ip*Ri + Un \qquad (I)$$

wherein $$Ip = (Uv - Un)/(Rv + Ri) \qquad (II)$$

Figure 3:
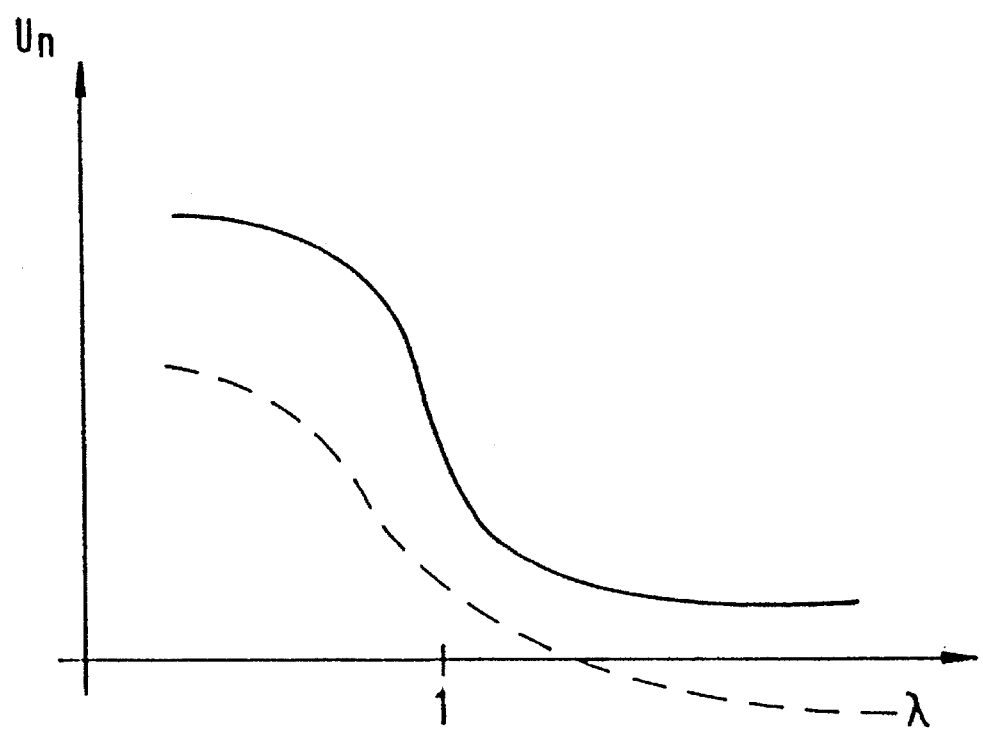
FIG. 3 is a graph which shows the change of output voltage of an oxygen concentration cell under the influence of an adulterated reference atmosphere.

The behavior of the source voltage Un of the exhaust-gas probe is made clear in FIG. 3 wherein the trace of the voltage Un is shown as a function of the air ratio λ of the mixture supplied to the engine. The solid line applies to a usual reference gas atmosphere having an oxygen partial pressure of typically 0.2 bar. In contrast to this reference pressure, the partial pressure of the equilibrium oxygen in the exhaust gas is lower by several powers of ten for each air ratio lambda and determines the amount and the direction of the Nernst voltage Un of the concentration cell. This Nernst voltage is positive over the entire lambda range in the exhaust gas of an internal combustion engine for driving motor vehicles.

The reference oxygen partial pressure is lowered in a reference atmosphere adulterated by fuel particles which have diffused thereinto. The resulting Nernst voltage is correspondingly decreased over the entire measuring range and can assume negative values especially in lean exhaust gas. The voltage trace shown by the broken line in FIG. 3 illustrates this case. Generally, for each concentration cell, the occurrence of a negative source voltage Un operated as a signal for the occurrence of an adulterated reference atmosphere and can be used to trigger a temporary pump current increase in order to regenerate this adulterated reference atmosphere as rapidly as possible.

Negative probe signals occur as shown in FIG. 3 preferably for lean mixture compositions. For this reason, a check of the probe signal can be made in the overrun mode of operation when metering of fuel is cut off. This operating state often continues over several seconds and thereby makes possible an especially reliable detection of an adulterated reference atmosphere since this can be noticed by a negative probe signal which is likewise maintained over several seconds.

If this case is determined by a check of the probe signal in the control apparatus 15, then this apparatus emits the signal SS which, for example, reduces the value of the series resistor Rv to approximately ⅕ of its otherwise valid value. Table 1 below shows the increase of the pump current Ip for a change of the series resistor Rv from 51 kohm to 10 kohm for rich (Un=0.9 Volt) and lean (Un=0.1 Volt) mixtures, respectively, for a probe internal resistance of 100 ohm. The values, which occur for these peripheral conditions for the pump current Ip and the probe voltage Us, are computed from the equations (I) and (II).

TABLE 1

Oxygen Probe having a Pumped Reference
Theoretical Values for Probe Voltage and Pump Current

| Ri [ohm] | Rv [kohm] | Uv [V] | Un | Us [V] | Ip [μA] |
|---|---|---|---|---|---|
| 100 | 51.0 | 1.0 | 0.9 | 0.900 | 2.0 |
| 100 | 51.0 | 1.0 | 0.1 | 0.102 | 17.6 |
| 100 | 10.0 | 1.0 | 0.9 | 0.901 | 9.9 |
| 100 | 10.0 | 1.0 | 0.1 | 0.109 | 89.1 |

For the exemplary values assumed here, the reduction of the series resistor Rv to approximately ⅕ of its value leads for continuous operation to an increase Of the pump current Ip and therefore to an increase of the oxygen ionic current to the reference gas volume by approximately a factor of 5. The time, which passes for eliminating the adulteration of the reference gas atmosphere, correspondingly shortens to approximately ⅕.

TABLE 2

Oxygen Probe having a Pumped Reference
Theoretical Values for Probe Voltage and Pump Current

| Ri [ohm] | Rv [kohm] | Uv [V] | Un | Us [V] | Ip [μA] |
|---|---|---|---|---|---|
| 100 | 51.0 | 1.0 | 0.9 | 0.900 | 2.0 |
| 100 | 51.0 | 1.0 | 0.1 | 0.102 | 17.6 |
| 100 | 51.0 | 3.0 | 0.9 | 0.904 | 41.1 |
| 100 | 51.0 | 3.0 | 0.1 | 0.106 | 56.8 |

Table 2 shows the effect of a change of the bias voltage Uv to threefold of its value, which is determined for continuous operation, in accordance with the embodiment of FIG. 1.

Here too, a significant increase of the pump current occurs.

The time duration in which the increased pump current is to flow, is dependent upon the characteristics of the exhaust-gas probe used.

On the one hand, the time integral of the pump current should be proportional to the reference gas volume since the integral is a measure for the pumped oxygen quantity which, for scavenging a larger reference gas volume, must be greater than for scavenging a comparatively smaller reference gas.

On the other hand, this integral should not lead to a significant decomposition of the electrolyte. In the simplest case, this integral results from the product of a constant increased pump voltage and the time. The corresponding values can be determined by experiments with the particular exhaust-gas probe of interest.

Figure 4:
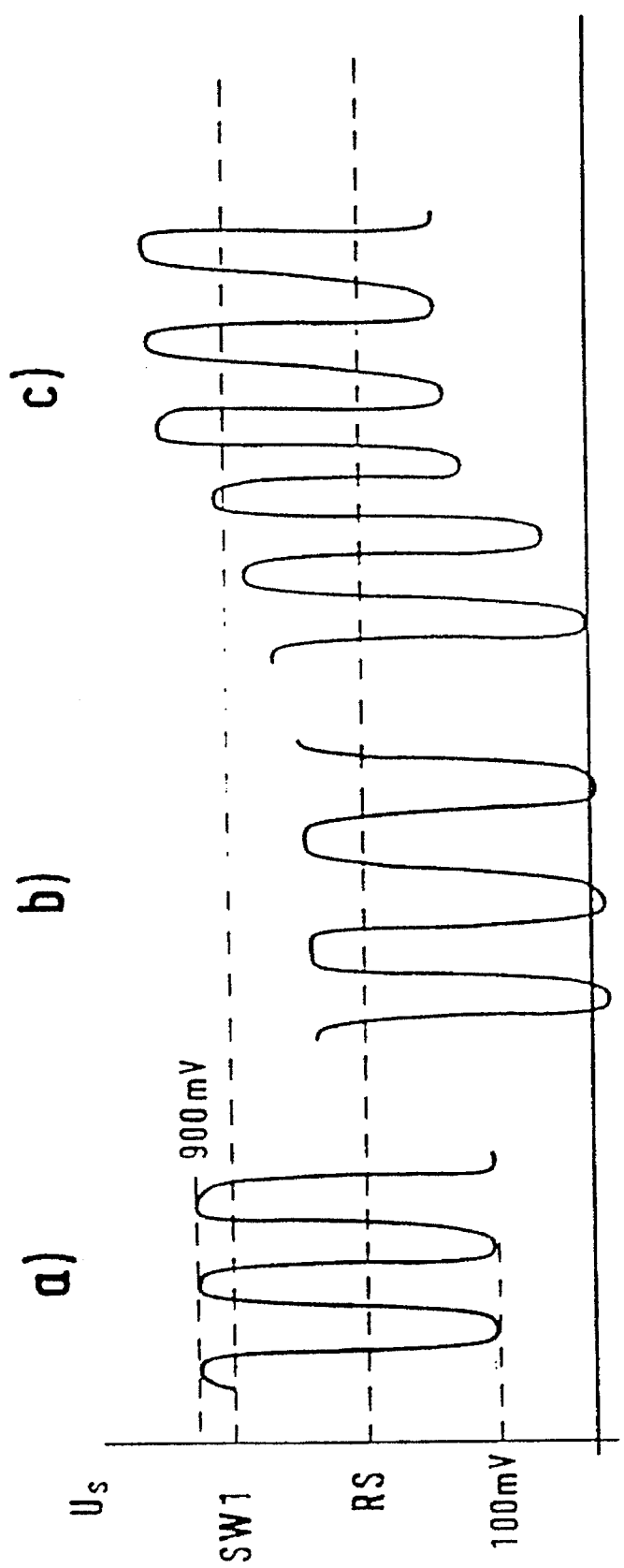
FIG. 4 shows the effect of the method of the invention on the output voltage of an exhaust-gas probe having a circuit as shown in FIGS. 1 or 2; and, FIG. 5 shows a flowchart for executing the method according to one embodiment of the invention.

The end of the pump current increase can also be triggered by a recovery of the probe signal Us. The time-dependent trace of this signal is shown in FIG. 4 in accordance with an embodiment of the method of the invention.

FIG. 4a shows the probe signal Us=Un+Ip*Ri as it oscillates in the case of an unadulterated reference between approximately 100 mV and 900 mV. The voltage shift Ip*Ri is approximately 1 mV as can be seen from Table 1 (Ri=100 ohm, Ip is approximately 10 μA as a mean value of 2 and 17.6 μA).

FIG. 4b shows the signal trace of Us in the case of the adulterated reference atmosphere. The drop of the Nernst voltage Un leads to the condition that a threshold value SW1 is no longer regularly passed through. This threshold value SW1 is greater than the control threshold RS and less than the probe voltage of 900 mV which is obtained regularly for an unadulterated reference. The pump current Ip is increased as a consequence of a corresponding inquiry in the control apparatus 15.

An increase by the factor 10 leads to a voltage offset Ri*Ip of approximately 10 mV. The direct influence of the pump current increase on the measured probe voltage Us is therefore comparatively small.

The indirect influence of the pump current increase becomes manifest in the recovery of the Nernst voltage Un which leads to the significant increase of the probe voltage Us to a value which is characteristic for an unadulterated reference atmosphere. This increase of the probe voltage Us is shown in FIG. 4c.

As a consequence of the foregoing, the threshold value SW1 is again run through which can be used as a switchoff criterion for the increased pump current.

Figure 5:
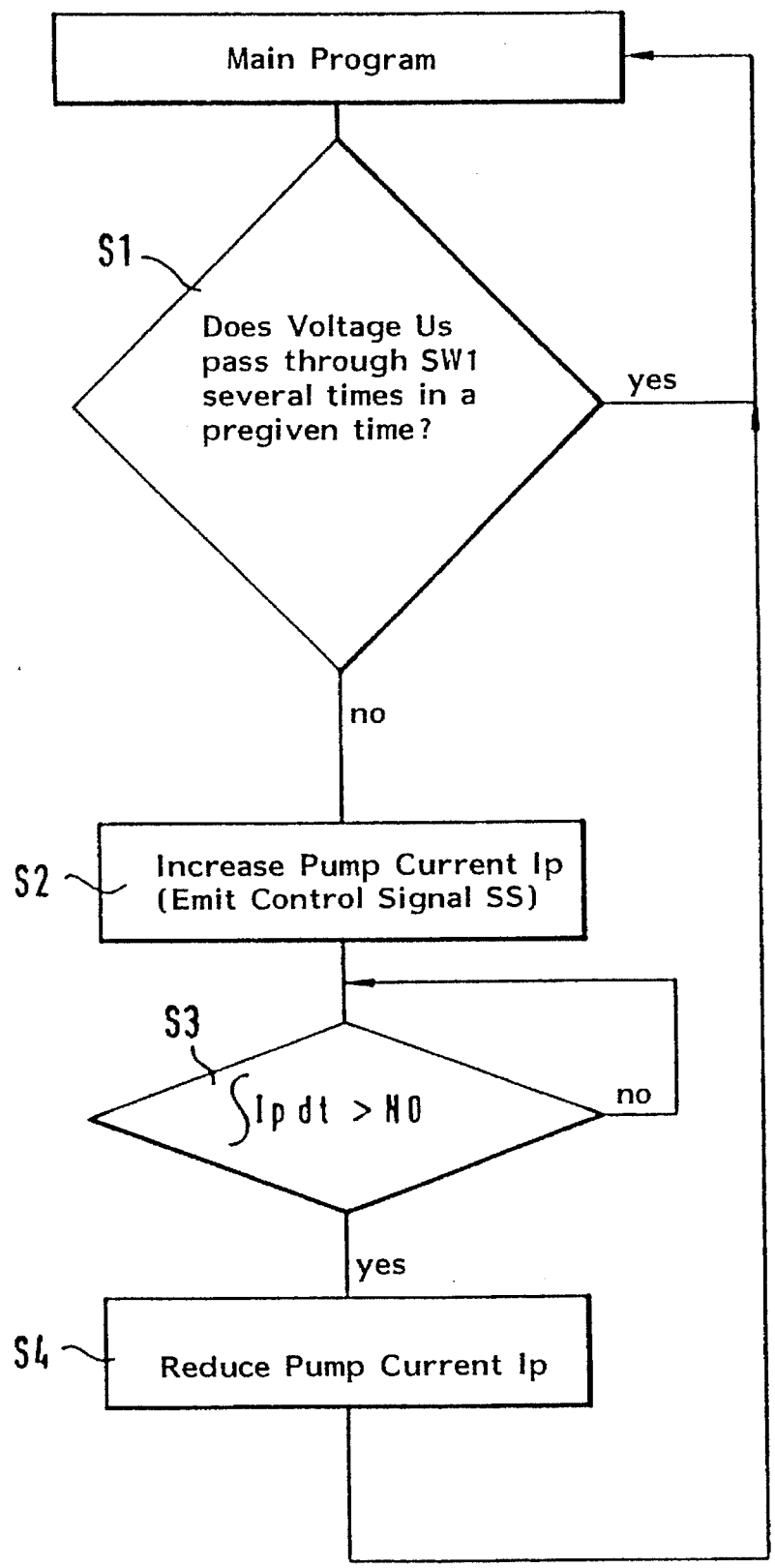

FIG. 5 shows a flowchart for carrying out the method of the invention and is triggered by a detection of the adulterated reference atmosphere. The following proceeds from a higher-ranking main program which serves, for example, for computing the injection pulses in the control apparatus 15. Proceeding from this program, a check is made in step S1 as to whether the voltage Us passes through the threshold value SW1 several times in a pregiven time such as within 10 seconds.

This inquiry is answered in the positive when the reference is unadulterated and a return is made to the main program without further measures. In contrast, a negative response leads to the output of signal SS for increasing the pump voltage or the pump current in step S2. In step S3, the time integral of the pump current is compared to a predetermined threshold value NO.

A reduction of the pump current or of the pump voltage is triggered in step S4 when this threshold value is exceeded and there is then a return to the main program.

Alternately to step S1, a check can be made as to whether the probe voltage assumes negative values in specific operating states such as in overrun operation. If this is the case, then the pump current is increased until the probe signal assumes positive values even in overrun operation and/or again passes through the threshold value SW1 outside of the overrun operation.

It is understood that the foregoing description is that of the preferred embodiments of the invention and that various changes and modifications may be made thereto without departing from the spirit and scope of the invention as defined in the appended claims.

What is claimed is:

1. A method of operating an exhaust-gas probe having an output voltage (Us) and including an oxygen-ion conducting solid electrolyte, a measuring electrode subjected to the exhaust gas of an internal combustion engine; holding means for holding a reference gas; and, a reference electrode subjected to said reference gas; said reference gas defining an internal reference by being partitioned off from the exhaust gas and the ambient so as to impede a particle exchange between said reference gas and the exhaust gas and/or the ambient; the method comprising the steps of:

continuously applying a voltage across said measuring and reference electrodes to have a predetermined magnitude and direction so as to cause a pump current (Ip) to flow between said electrodes for transporting oxygen ions from said measuring electrode to said reference electrode without causing said electrolyte to decompose under the action of the continuously applied voltage;

temporarily increasing said pump current (Ip) for a first time duration to values which would lead to a decomposition of said electrolyte if allowed to act on said electrolyte over a second time duration greater than said first time duration; and, triggering said temporary increase in said pump current (Ip) after each start of said engine or after a pregiven duration of operation of said engine and/or when a drop of the output voltage (Us) of said exhaust-gas probe indicates said reference gas as being adulterated.

2. The method of claim 1, further comprising the step of triggering said temporary increase of said pump current (Ip) when said output voltage Us does not pass through a pregiven threshold value (SW1) within a pregiven time span at least once.

3. The method of claim 1, further comprising the step of forming the product of said first time duration and the magnitude of the increase in said pump current (Ip) and matching said product to the magnitude of a volume of said reference gas.

4. A combination of an exhaust-gas probe having an output voltage and a current supply for operating the exhaust-gas probe, the combination comprising:

said exhaust-gas probe including:

a solid electrolyte for conducting oxygen ions; subjected to the exhaust gas to be measured and said exhaust gas a measuring electrode arranged on said electrolyte and containing gas particles;

said electrolyte including holding means for holding a reference gas containing gas particles and said reference gas defining an internal reference;

means for separating said reference gas from the exhaust gas and the ambient air containing gas particles so that an exchange of gas particles between said reference gas and said exhaust gas and/or the ambient air is impeded; and, a reference electrode disposed in said electrolyte so as to be subjected to said reference gas;

a current supply for continuously applying a voltage across said electrodes to have a predetermined magnitude and direction so as to cause a pump current (Ip) to flow between said electrodes which transports oxygen ions from said measuring electrode to said reference electrode without causing said electrolyte to decompose under the action of the continuously applied voltage; and, said current supply including means for increasing said pump current (Ip) temporarily for a first time duration to values which would lead to a decomposition of said electrolyte if allowed to act on said electrolyte over a second time duration greater than said first time duration, said means for increasing the pump current temporarily being adapted to be triggered by each start of an internal combustion engine producing said exhaust gas or after a pregiven duration of operation of said engine and/or when a drop of said output voltage of the exhaust gas probe indicates said reference gas as being adulterated.

5. The combination of claim 4, said current supply including: a first voltage source for supplying a pump current which flows via the exhaust-gas probe in normal operation; and, a second voltage source which operates to temporarily increase said pump current.

6. The combination of claim 4, said current supply including a voltage source and said means for temporarily increasing said pump current (Ip) being an adjustable resistor.

7. The combination of claim 4, said electrolyte including a channel made of porous material for connecting said holding means and said reference gas to the ambient.

8. The combination of claim 4, wherein said solid electrolyte is a measuring cell; and, the combination further includes additional cells in combination with said exhaust-gas probe.

* * * * *